(12) United States Patent
Wei et al.

(10) Patent No.: US 6,608,916 B1
(45) Date of Patent: Aug. 19, 2003

(54) AUTOMATIC DETECTION OF SPINE AXIS AND SPINE BOUNDARY IN DIGITAL RADIOGRAPHY

(75) Inventors: Guo-Qing Wei, Plainsboro, NJ (US); Jianzhong Qian, Princeton, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 429 days.

(21) Appl. No.: 09/638,120

(22) Filed: Aug. 14, 2000

(51) Int. Cl.[7] .............................. G06K 9/00; G06K 9/48
(52) U.S. Cl. .......................................... 382/132; 382/199
(58) Field of Search ................................. 382/128, 132, 382/199, 202, 203, 266, 141, 152, 205, 263, 291; 128/922

(56) References Cited

U.S. PATENT DOCUMENTS 6,539,099 B1 * 3/2003 Kellner ........................ 382/103

OTHER PUBLICATIONS

Claude Kauffman et al., "Digital Radiography Segmentation of Scoliotic Vertebral Body Using Deformable Models," SPIE vol. 3034.

B. Verdonck et al., "Computer Assisted Quantitative Analysis of Deformities of the Human Spine," pp. 822–831, 1998.

* cited by examiner

*Primary Examiner*—Brian Werner
*Assistant Examiner*—Ryan J. Miller
(74) *Attorney, Agent, or Firm*—Donald B. Paschburg

(57) ABSTRACT

A system and method for automatically detecting a spinal axis and spinal boundaries from an image, in accordance with the present invention, includes scanning an input image in at least two scan directions to generate a ridge map associated with each scan direction. The ridge maps are fused to enhance a projected spinal axis. A piece-wise linear approximation of the projected spine axis is provided, and a gradient map of the input image is enhanced project spine boundaries. Spine boundaries are determined by constraining the projected spine boundaries relative to each other and the spine axis.

22 Claims, 3 Drawing Sheets spine axis spine axis

AUTOMATIC DETECTION OF SPINE AXIS AND SPINE BOUNDARY IN DIGITAL RADIOGRAPHY

BACKGROUND

1. Technical Field

This disclosure relates to digital radiography, and more particularly to fully automatic detection of a spine axis and spine boundary in digital radiography.

2. Description of the Related Art

With the development of digital imaging technologies, the interest in using computers for assisting deformity analysis of scoliotic spines in radiography is increasing. Currently, most of these measurements are manually made. Manual measurement is not only time-consuming, but also subject to errors depending on the person's skill, experience and other human factors.

Spine axis and spine boundaries are important anatomies that are not only components for deformity measurement but also the reference positions used for the deformity quantification from many other anatomic landmarks. Existing algorithms for detecting spine axis and spine boundary require human interaction. Usually a set of control points is needed to be placed manually on the spine axis.

Kauffmann and Guise, in "Digital Radiography Segmentation of Scoliotic Vertebral Body Using Deformable Models", *Proceedings of SPIE-Medical Imaging*, Vol. 3034, pp. 243–251, 1997, used a cubic curve to interpolate a set of manually placed control points to determine the axis of the spine. A method, called "active contour", is applied to detect each vertebra. The spine boundary is found by simply connecting the boundaries of the detected vertebrae. Since the active contour method is sensitive to image noise, the success of the method depends on the image quality and the success of the detection of individual vertebrae.

Verdonck et al., in "Computer Assisted Quantitative Analysis of Deformities of the Human Spine", *Proceedings of Medical Image Computing and Computer Assisted Intervention*, pp. 822–831, 1998, used a poly-Bezier curve for the interpolation of the spine axis from a set of manually placed control points, with the possibility of interactive editing of the interpolation. The spine boundaries are found by linking strong edges on each side of the spine axis. Since strong edges not belonging to the spine boundary may interfere with the linking process, the boundaries thus determined may appear unsmooth, noise-corrupted, and sometimes contain errors.

Therefore, a need exists for a stable detection method that requires no human interaction. A further need exists for a method where the placement of control points on the spine axis is unnecessary. A still further need exists for a method, which integrates domain-specific knowledge about the spine shape into the detection process in a systematic way, so that errors can be avoided at the very early stage of detection.

SUMMARY OF THE INVENTION

A system and method for automatically detecting a spinal axis and spinal boundaries from an image, in accordance with the present invention, includes scanning an input image in at least two scan directions to generate a ridge map associated with each scan direction. The ridge maps are fused to enhance a projected spinal axis. A piece-wise linear approximation of the projected spine axis is provided, and a gradient map of the input image is enhanced project spine boundaries. Spine boundaries are determined by constraining the projected spine boundaries relative to each other and the spine axis.

Another method for automatically detecting a spinal axis and spinal boundaries from an image, includes the steps of providing an input image of a spine, scanning the input image in at least two scan directions to generate a ridge map associated with each scan direction, fusing the ridge maps to enhance a projected spinal axis, providing a piece-wise linear approximation of the projected spine axis, enhancing a gradient map of the input image to highlight projected spine boundaries associated with the linear approximation of the projected spine axis, providing a piece-wise linear approximation of the projected spine boundaries, and constraining the projected spine boundaries relative to each other and the projected spine axis to determine spine boundaries.

In other methods, the step of providing a piece-wise linear approximation of the projected spine axis may include the steps of cutting an image of the projected spine axis into segments by employing a plurality of equally spaced cutting lines and determining endpoints of the segments to approximate the spine axis as piece-wise linear segments. The method may include the step of constraining the segments by considering angular relationships among the segments and projection strength of the segments.

In still other methods, the step of determining the spine boundaries may include the steps of cutting the gradient map of the projected spine boundaries into segments by employing a plurality of equally spaced cutting lines and defining endpoints of the segments at intersections between the cutting lines and the projected spine boundaries wherein the segments are approximated as lines. Constraining the projected spine boundaries may further include the step of constraining the segments by considering angular relationships among the segments, distances between adjacent segments and projection strength of the segments.

The step of generating an updated spine axis from the spinal boundaries may be included. The step of determining the spine boundaries may include employing a dual dynamic programming procedure for detecting the spinal boundaries. The method may include the step of downsizing and smoothing the input image. The above methods may be implemented by a program storage device readable by machine, tangibly embodying a program of instructions executable by the machine to perform these method steps.

These and other objects, features and advantages of the present invention will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF PREFERRED EMBODIMENTS

The present invention provides a fully automatic detection of the spine axis and spine boundary in digital radiography. The detection procedure does not require user interventions, such as the placement of a set of control points by humans, as conventional methods do. A path projection method is provided to find a piecewise linear approximation of the spine axis and boundaries. Prior knowledge can be integrated into the detection procedure to enable a stable and accurate detection. These detected anatomical landmarks include information for further automatic quantitative analysis, disease diagnosis, and surgery planning.

The present invention extracts useful information about the spine position from a downsized and smoothed spine image in different scales, where irrelevant information is automatically suppressed. Extracted position information is then propagated to finer image resolutions as the constraints in the subsequent localization of the boundaries. At the same time, knowledge about the spine shape, such as the range of orientation and the extent of possible bending (e.g., due to the pathology of spines, scoliosis, other diseases, etc.), is incorporated into the procedure to both restrict the space of admissible solutions and to increase the reliability of the detection. This is made possible by a projected-path based optimization method, which is included in the present invention.

Figure 1:
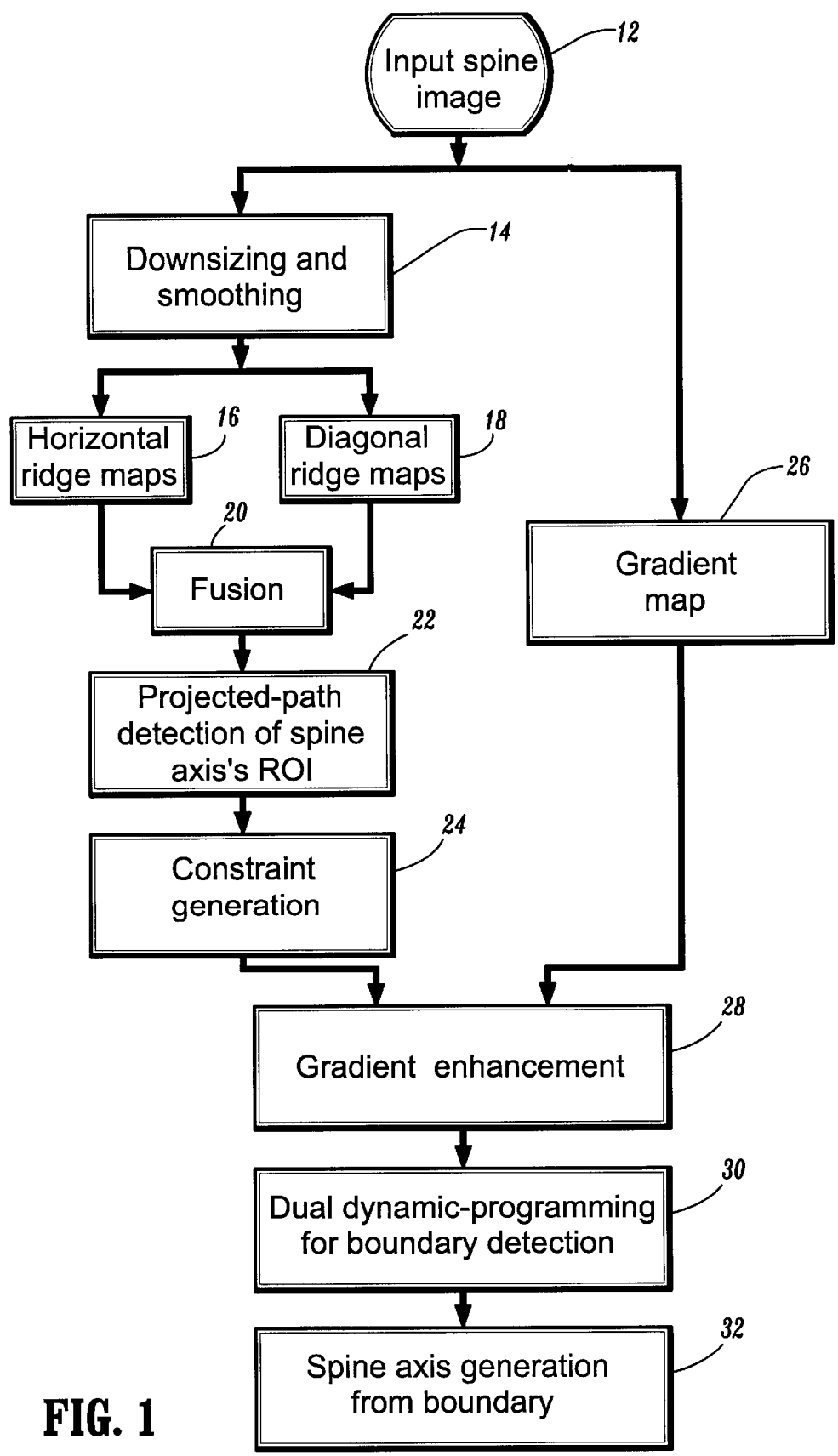
FIG. 1 is a block/flow diagram showing a detection system/method in accordance with one embodiment of the present invention.

It should be understood that the elements shown in FIG. 1 may be implemented in various forms of hardware, software or combinations thereof. Preferably, these elements are implemented on one or more appropriately programmed general purpose digital computers having a processor and memory and input/output interfaces. Referring now in specific detail to the drawings in which like reference numerals identify similar or identical elements throughout the several views, and initially to FIG. 1, a block/flow diagram is shown for a detection method in accordance with one embodiment of the present invention. Although this disclosure employs the illustrative example of spine position, the methods and system described herein may be employed for tracking and defining other anatomical features, structures or organs. For example, the detection method of the present invention may be employed for planning surgical procedures for setting fractured or broken bones.

In block 12, an image is input for processing. The image, in this example, includes an image of a spine taken by X-ray or other imaging technologies, such as computerized axial tomography (e.g., CAT scan), sonogram, magnetic resonance (MRI) or other techniques. The image is preferably converted or taken in digital form. In block 14, the digital image is downsized and smoothed. Downsizing may include employing compression algorithms known in the art. Smoothing the image may also be performed by employing known techniques. In blocks 16 and 18, from the downsized and smoothed image, intensity ridges of different preferred scan orientations are extracted and fused together in block 20. In this example, the scan orientation chosen includes horizontal and diagonal orientations, any other orientation may also be employed.

The ridge images are obtained by scanning across the image in specified directions and computing curvatures of intensity profiles in the specified directions at each pixel. At positions where there are ridges in the original image, the ridge image appears brighter. This ridge computation is performed in at least two scanning orientations. The at least two images (maps) are fused together to provide a resultant image or ridge map in block 20.

Figure 2:
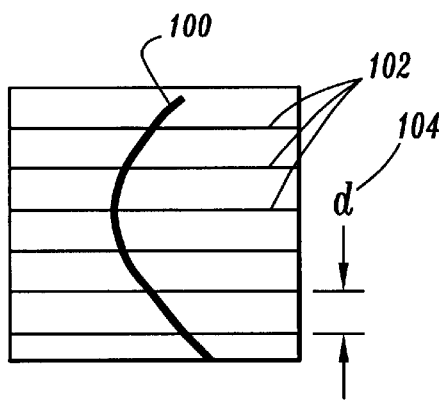
FIG. 2 is a schematic diagram showing cutting lines for segmenting a projected spine axis in accordance with the present invention.

In block 22, the obtained ridge image or images are employed to detect a projected spine axis path. (Here only an approximate position of the spine axis is detected, e.g., spine axis region of interest. As shown in FIG. 2, a region of interest (ROI) 100 in the ridge image at the projected spine axis path is divided into several parts in the same direction by cutting lines 102 which are separated by a pre-selected step size 104.

Figure 3:
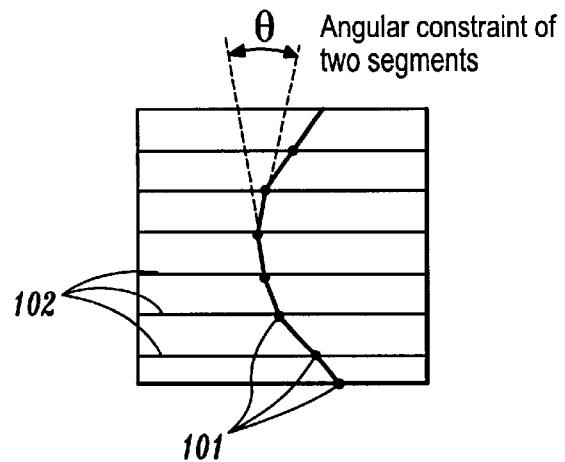
FIG. 3 is a schematic diagram showing a piece-wise linear approximation of the projected spine axis with constraints in accordance with the present invention.

Referring to FIG. 3, choosing one point 101 on each of the horizontal cutting lines 102 constitutes a piecewise linear approximation of the spine axis. Factors affecting the point selection include the orientations of the line segments, the angle between successive segments, and the strength of the ridges where the segments run through, which is measured as the projection of the ridge map along the path. The method for choosing the point on each horizontal cutting line while taking into account the above constraints is based on dynamic programming, which is a preferred optimization approach. Dynamic programming algorithms are known in the art.

In block 24, constraints are generated based on the position of the detected spine axis's ROI. These constraints include the position range and orientation range of the spine boundary.

In block 26, a gradient map is provided from the input image of block 12. A gradient map is computed based on the intensity differences in the horizontal and vertical directions, and the gradient map measures the rate of intensity change around each pixel. The gradient map highlights intensity edges in the input image. Using the spine axis (block 24) and the gradient map (block 26), in block 28, image gradients in the orientation of the spine axis are enhanced. The filtering or enhancement removes some pixels which are less likely stemming from the spine boundary.

Figure 4:
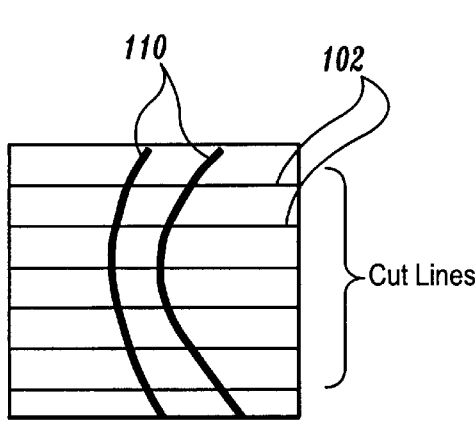
FIG. 4 is a schematic diagram showing cutting lines for segmenting a projected spine boundaries in accordance with the present invention.
Figure 5:
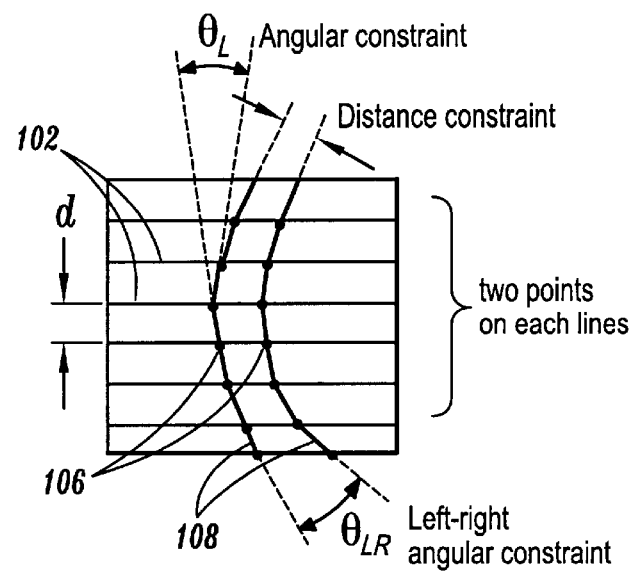
FIG. 5 is a schematic diagram showing a piece-wise linear approximation of the projected spine boundaries with constraints in accordance with the present invention.

As shown in FIG. 4, an enhanced gradient image (to determine projected boundaries of the spine) 110 is cut by cutting lines 102 similarly to the ridge map as described above. As shown in FIG. 5, a piecewise linear approximation of a spine boundary 108 is obtained by selecting two points 106 on each of the cut lines 102. The ranges of the two points are confined to the neighboring spine axis (see FIG. 2) found previously. Other constraints for the point selection consider not only the angular relationships among the segments ($\hbar_L$ and $\hbar_{LR}$) and the projection strength (e.g., the strength of the enhanced gradient map) along the segments, but also the distances (d) between the segments.

In block 30, a dual dynamic-programming procedure is employed to constrain the spinal boundaries. The dual dynamic-programming procedure integrates two dynamic programming optimizations (one for each boundary) into a single optimization and permits the optimizations to interact and constrain each other. The dual dynamic-programming procedure includes horizontal coordinates on all cutting lines as the state variables. The state variables are ordered according to the cutting line number from bottom to top. Since the cutting lines divide the spinal boundary into segments of boundaries (each segment includes a left side part and a right side part). The scores for all possible positions can be computed for the whole spinal boundary (governed by the state variables) by a successive computational scheme.

First, the scores for the lowest boundary segment are computed. Then, the scores, after adding one segment, are computed based on the already computed scores for the previous segment, the gradient strength for the current segment and geometric constraints between the current segment(s) and previous segment(s). This procedure is repeated until all the scores for the whole spinal boundary are computed. Then, the maximum score is chosen for the scores to determine the position of the spinal boundary.

In block 32, after boundary detection, a more accurate position of the spine axis is computed from the spine boundary. This may be performed by determining a locus of points equidistant form the adjacent boundary lines or by weighting the spinal axis in connection with other factors (e.g., curvature, etc.).

Figure 6A:
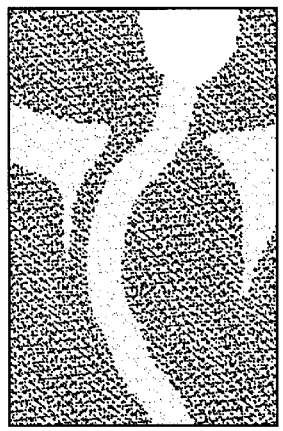
FIG. 6a depicts a spine image to be employed with he present invention.
Figure 6B:
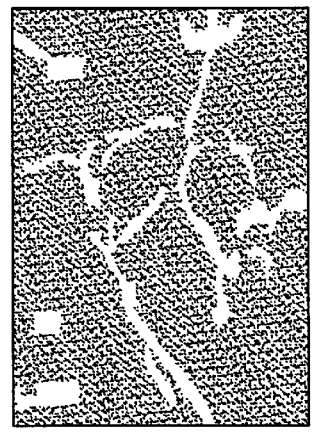
FIG. 6b depicts a fused ridge map in accordance with the present invention.
Figure 6C:
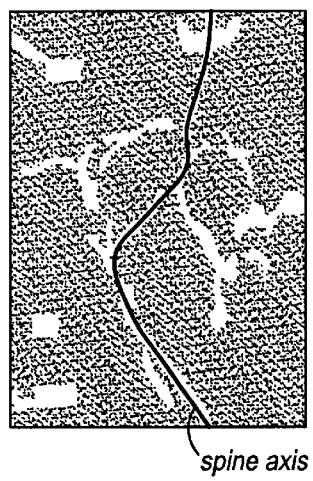
FIG. 6c depicts the fused ridge map. of FIG. 6b with a detected spine axis in accordance with the present invention.
Figure 6D:
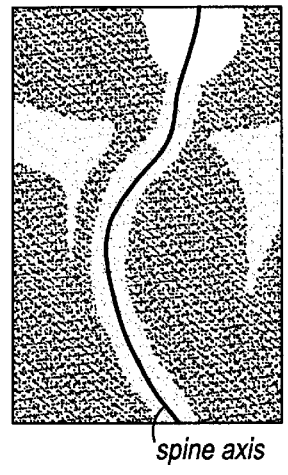
FIG. 6d depicts the detected spine axis of FIG. 6c overlaid on the spine image of FIG. 6a in accordance with the present invention.
Figure 6E:
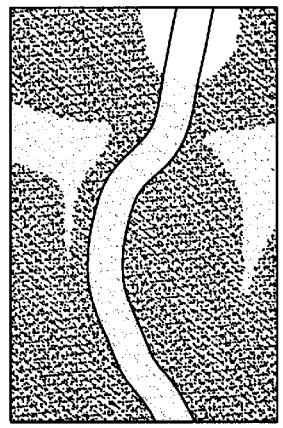
FIG. 6e depicts detected spine boundaries in accordance with the present invention.

Referring to FIGS. 6a–e, an example of the detection of spinal boundaries is shown in accordance with the present invention. In FIG. 6a, a spine image is provided by a digitally rendered X-ray image. In FIG. 6b, a ridge map is depicted, which is generated by scanning the spine image of FIG. 6a. In FIG. 6c, a spine axis has been detected from the ridge map of FIG. 6b. In FIG. 6d, the spine image is overlaid with the spine axis determined in FIG. 6c to demonstrate the actual position of the spine in the image. In FIG. 6e, a spine boundary is detected and overlaid on the spine image.

The detected spine axis and boundary then can be used for further automatic quantitative analysis, disease diagnosis, and surgery planning. The spine boundary and axis may also serve as the automatic region-of-interest definition for the detection of other anatomies and may be used for example, for the measurement of spinal deformity, etc.

Having described preferred embodiments for automatic detection of spine axis and spine boundary in digital radiography for deformity analysis using dual dynamic programming and path projections (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A method for automatically detecting a spinal axis and spinal boundaries from an image, comprising the steps of:

scanning an input image in at least two scan directions to generate a ridge map associated with each scan direction;

fusing the ridge maps to enhance a projected spine axis;

providing a piece-wise linear approximation of the projected spine axis;

enhancing a gradient map of the input image to highlight pixels lying on projected spine boundaries; and determining the spine boundaries by constraining the projected spine boundaries relative to each other and the spine axis.

2. The method as recited in claim 1, wherein the step of providing a piece-wise linear approximation of the projected spine axis includes the steps of:

cutting an image of the projected spine axis into segments by employing a plurality of equally spaced cutting lines; and determining endpoints of the segments to approximate the spine axis as piece-wise linear segments.

3. The method as recited in claim 2, further comprising the step of constraining the segments by considering angular relationships among the segments and projection strength of the segments.

4. The method as recited in claim 1, wherein the step of determining the spine boundaries includes the steps of:

cutting the gradient map of the projected spine boundaries into segments by employing a plurality of equally spaced cutting lines; and defining endpoints of the segments at intersections between the cutting lines and the projected spine boundaries wherein the segments are approximated as lines.

5. The method as recited in claim 4, wherein defining endpoints further comprises the step of constraining the segments by considering angular relationships among the segments, distances between adjacent segments and projection strength of the segments.

6. The method as recited in claim 1, further comprising the step of generating an updated spine axis from the spinal boundaries.

7. The method as recited in claim 1, wherein the step of determining the spine boundaries includes employing a dual dynamic programming procedure for detecting the spinal boundaries.

8. A method for automatically detecting a spinal axis and spinal boundaries from an image, comprising the steps of:

providing an input image of a spine;

scanning the input image in at least two scan directions to generate a ridge map associated with each scan direction;

fusing the ridge maps to enhance a projected spinal axis;

providing a piece-wise linear approximation of the projected spine axis;

enhancing a gradient map of the input image to highlight pixels lying on projected spine boundaries associated with the linear approximation of the projected spine axis;

providing a piece-wise linear approximation of the projected spine boundaries; and constraining the projected spine boundaries relative to each other and the projected spine axis to determine spine boundaries.

9. The method as recited in claim 8, wherein the step of providing a piece-wise linear approximation of the projected spine axis includes the steps of:

cutting an image of the projected spine axis into segments by employing a plurality of equally spaced cutting lines; and determining endpoints of the segments to approximate the spine axis as piece-wise linear segments.

10. The method as recited in claim 8, further comprising the step of constraining the segments by considering angular relationships among the segments and projection strength of the segments.

11. The method as recited in claim 8, wherein the step of providing a piece-wise linear approximation of the projected spine boundaries includes the steps of:

cutting the gradient map of the projected spine boundaries into segments by employing a plurality of equally spaced cutting lines; and determining endpoints of the segments at intersections between the cutting lines and the projected spine boundaries wherein the segments are approximated as lines.

12. The method as recited in claim 11, wherein the step of constraining the projected spine boundaries further comprises the step of constraining the segments by considering angular relationships among the segments, distances between adjacent segments and projection strength of the segments.

13. The method as recited in claim 8, further comprising the step of generating an updated spine axis from the spinal boundaries.

14. The method as recited in claim 8, wherein the step of constraining the projected spine boundaries includes employing a dual dynamic programming procedure for detecting the spinal boundaries.

15. The method as recited in claim 8, further comprising the step of downsizing and smoothing the input image.

16. A program storage device readable by machine, tangibly embodying a program of instructions executable by the machine to perform method steps automatically detecting a spinal axis and spinal boundaries from an image, the method steps comprising:

scanning an input image in at least two scan directions to generate a ridge map associated with each scan direction;

fusing the ridge maps to enhance a projected spinal axis;

providing a piece-wise linear approximation of the projected spine axis;

enhancing a gradient map of the input image to highlight projected spine boundaries; and determining the spine boundaries by constraining the projected spine boundaries relative to each other and the spine axis.

17. The program storage device as recited in claim 16, wherein the step of providing a piece-wise linear approximation of the projected spine axis includes the steps of:

cutting an image of the projected spine axis into segments by employing a plurality of equally spaced cutting lines; and determining endpoints of the segments to approximate the spine axis as piece-wise linear segments.

18. The program storage device as recited in claim 17, further comprising the step of constraining the segments by considering angular relationships among the segments and projection strength of the segments.

19. The program storage device as recited in claim 17, wherein the step of determining the spine boundaries includes the steps of:

cutting the gradient map of the projected spine boundaries into segments by employing a plurality of equally spaced cutting lines; and defining endpoints of the segments at intersections between the cutting lines and the projected spine boundaries wherein the segments are approximated as lines.

20. The program storage device as recited in claim 19, wherein constraining the projected spine boundaries further comprises the step of constraining the segments by considering angular relationships among the segments, distances between adjacent segments and projection strength of the segments.

21. The program storage device as recited in claim 17, further comprising the step of generating an updated spine axis from the spinal boundaries.

22. The program storage device as recited in claim 17, wherein the step of determining the spine boundaries includes employing a dual dynamic programming procedure for detecting the spinal boundaries.

* * * * *